US 6,455,302 B1

(12) United States Patent
Uhm et al.

(10) Patent No.: US 6,455,302 B1
(45) Date of Patent: *Sep. 24, 2002

(54) METHOD FOR OPTICALLY RESOLVING A RACEMIC α-SUBSTITUTED HETEROCYCLIC CARBOXYLIC ACID USING ENZYME

(75) Inventors: Ki-Nam Uhm; Sang-Chul Lim; Jong-Ho Lim, all of Taejon (KR)

(73) Assignee: SK Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 09/871,360

(22) Filed: May 31, 2001

(30) Foreign Application Priority Data

Jun. 1, 2000 (KR) .............................................. 00-30068
Jun. 1, 2000 (KR) .............................................. 00-30069

(51) Int. Cl.$^7$ .................................................. C07F 9/00

(52) U.S. Cl. .................................................... 435/280

(58) Field of Search ........................................ 435/280

(56) References Cited

U.S. PATENT DOCUMENTS 5,928,933 A    7/1999   Dicosimo et al. ........... 435/280

FOREIGN PATENT DOCUMENTS

JP           1216983         8/1989
JP            971576         3/1997

Primary Examiner—Sandra E. Saucier
Assistant Examiner—Vera Afremova
(74) Attorney, Agent, or Firm—Abelman, Frayne & Schwab

(57) ABSTRACT

Disclosed is a method for optically resolving a racemic α-substituted heterocyclic carboxylic acid (α-HCCA) by taking advantage of enantioselectivity of enzymes. α-HCCA is reacted with alcohol to give a racemic α-HCCA ester, which is then reacted with an enzyme with enantioselectivity, whereby either R-form or S-form of the racemate is hydrolyzed. Extraction with an organic solvent can obtain enantiomers of the α-HCCA ester. The extracted enantiomeric α-HCCA ester is converted to enantiomeric α-HCCA by catalytic hydrogenation in an organic solution or by enzymatic hydrolysis in an aqueous solution. Thus, a racemic mixture of α-HCCA can be optically resolved with high optical purity at high yields as well as at low cost.

15 Claims, No Drawings

METHOD FOR OPTICALLY RESOLVING A RACEMIC α-SUBSTITUTED HETEROCYCLIC CARBOXYLIC ACID USING ENZYME

BACKGROUND OF THE INVENTION

1. Field of the Invention

The present invention relates to a method for optically resolving a racemic α-substituted heterocyclic carboxylic acid (hereinafter referred to as "α-HCCA"). More particularly, the present invention pertains to a method for optically resolving a racemic α-HCCA using an enzyme catalyst with enantioselectivity.

2. Description of the Prior Art

Divided into optical isomers, R- and S-forms, tetrahydro-2-furoic acid (hereinafter referred to as "THFA"), a kind of α-HCCA, is an important chiral building block which has various applications in chemistry. Of the optical isomers, R-(+)-THFA is used as a side chain intermediate for the synthesis of penem type antibiotics while S-(−)-THFA is useful as a chiral intermediate for organic synthesis. Therefore, THFA is different in use in R form and S form thereof. However, because THFA is obtained in the form of a racemic mixture when chemically synthesized, additional processes are required to separate THFA into enantiomers thereof: R and S forms.

Optical resolution has been usually used to divide racemic THFA into R- and S-forms thereof. In 1983, Belanger successfully separated THFA racemate into enantiomers thereof by use of brucine and ephedrine as resolving agents (Can. J. Chem., 61, 1383 (1983)). However, the resolving agents are not economical because of their being very expensive. Another problem with this process is that its products are low in enantiomeric excess value.

Japanese Pat. Laid-Open Publication No. 89-216983 discloses the use of a chiral amine (1-(4-halogenophenyl) ethylamine) as a resolving agent, in which diastereomer salts are prepared from R,S-THFA and optically resolved. This method is also economically unfavorable owing to the high price of the chiral amine. Additionally, only low production yields can be obtained because the amount of R,S-THFA to be added in the early reaction is limited to as low as 4 mmol. Furthermore, the chiral THFA finally obtained is poor in enantiomeric excess value.

A method different from optical resolving methods is found in Japanese Pat. Laid-Open Publication. No. 97-71576 which refers to synthesizing R- or S-THFA by treating R- or S-THFA salts with hydrogen halide.

It has been well known for some time that optical resolution of racemates could be achieved by use of enzymes, such as esterases, lipases, and proteases, as enzyme catalysts to enantioselectively hydrolyze one of the two enantiomers present. For example, U.S. Pat. No. 5,928,933 discloses an enzyme with an enantiomeric excess of 95% as a result of extensive experiments for reaction specificity of 44 enzymes, including proteases, lipases and esterases. The enzyme catalyst is very useful for the separation of enantiomeric racemates, but because the selectivity for enantiomers and the optical purity of products may vary depending on the choice of enzymes and chemical structures of their substrates, intensive efforts are required to find combinations of enzymes suitable for substrates. Especially, nowhere is found a method for optical resolution of α-HCCA using an enzyme.

Therefore, there remains a need for an enzymatic optical resolution method that can divide racemic α-HCCA into R- and S-form economically and easily.

SUMMARY OF THE INVENTION

Leading to the present invention, the intensive and through research on the optical resolution of α-HCCA, conducted by the present inventors aiming to develop optically highly pure α-HCCA by an economical procedure, resulted in the finding that some of microorganism- or animal-derived hydrolyzing enzymes may enantioselectively hydrolyze the ester functionality of particular optical isomers of α-HCCA at high efficiency.

Therefore, it is an object of the present invention to overcome the above problems encountered in prior arts and to provide a method for optically resolving a racemic α-HCCA using an enzyme, which is economically favorable.

In one aspect of the present invention, there is provided a method for optically resolving a racemic α-HCCA, comprising the steps of:

reacting a racemic α-HCCA with alcohol to give a racemic α-HCCA ester represented by the following chemical formula 1:

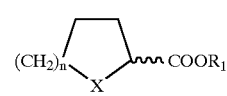

wherein $R_1$ is selected from the group consisting of substituted or unsubstituted alkyl or alkenyl containing 1 to 6 carbon atoms, benzyl, cycloalkyl containing 3 to 6 carbon atoms, substituted or unsubstituted arylalkyl, and substituted or unsubstituted heteroarylalkyl, X represents O, S or N—H, and n is an integer of 1 to 3;

optically resolving the racemate of the formula 1 by use of an enzyme with enantioselectivity to hydrolyze either R-form or S-form of the ester racemate thereby producing a R-form or S-form of α-HCCA and a counter enantiomeric form of α-HCCA ester thereto, said enzyme existing as a powder or an aqueous solution;

extracting the unhydrolyzed α-HCCA ester with an organic solvent; and subjecting the extracted α-HCCA ester in an organic solvent to hydrogenation under a constant hydrogen partial pressure at a constant temperature in the presence of a palladium catalyst on carbon (Pd/C).

In another aspect of the present invention, there is provided a method for optically resolving a racemic α-HCCA, comprising the steps of:

reacting a racemic α-HCCA with alcohol to give a racemic α-HCCA ester represented by the chemical formula 1;

optically resolving the racemate of the formula 1 by use of an enzyme with enantioselectivity to hydrolyze either R-form or S-form of the ester racemate, thereby producing a R-form or S-form of α-HCCA and a counter enantiomeric form of α-HCCA ester thereto, said enzyme existing as a powder or an aqueous solution;

extracting the unhydrolyzed α-HCCA ester with an organic solvent; and treating the extracted α-HCCA ester with a non-enantioselective enzyme in an aqueous solution at a constant pH and temperature, said enzyme existing as a powder or an aqueous solution.

DETAILED DESCRIPTION OF THE INVENTION

The present invention is characterized by the enantioselective hydrolysis of esters of racemic α-HCCA by an enzyme to produce a certain enantiomeric form of α-HCCA and a counter enantiomeric form of the esters of α-HCCA, at once. The separation of the hydrolyzed α-HCCA and the remaining esters of α-HCCA can be achieved by use of an organic solvent. The unhydrolyzed enantiomeric form of α-HCCA ester can be hydrolyzed in the presence of non-enantioselective enzyme or be hydrogenated in the presence of a palladium catalyst on carbon (Pd/C) to obtain the corresponding α-HCCA thereto.

In detail, a racemic mixture of α-HCCA is reacted with an alcohol at an equivalent amount to produce a racemic mixture of an α-HCCA ester, which is then enantioselectively hydrolyzed at a constant temperature and pH in an aqueous solution in the presence of an enzyme with enantioseletivity. As a result, the reaction produces an R- or S-form α-HCCA, along with the ester of α-HCCA which has an enantiomeric form counter to that of the hydrolyzed α-HCCA. After completion of the enantioselective hydrolysis, addition of an organic solvent extracts the ester of α-HCCA thereinto, leaving the α-HCCA in the aqueous phase only. Removal of the organic solvent from the organic phase results in acquisition of an optically pure S- or R-form of α-HCCA ester. Poor in optical purity, the α-HCCA remaining in the aqueous solution may be increased in purity through a purification process using, for example, a column, or may be reused as a starting material in the present invention.

In accordance with a preferred embodiment of the present invention, THFA, which belongs to an (α-HCCA, is used as a starting material and after optical resolution, R- or S-form of THFA can be obtained at a high enantiomeric excess. Aside from THFA, all materials falling within the scope of α-HCCA, for example, proline and tetrahydrothiopen-2-carboxylic acid can be optically resolved in accordance with the present invention.

Useful in the present invention are linear or branched C1–C6 alcohols, aromatic alcohols, C3–C6 cycloalkyl alcohols, substituted or unsubstituted arylalkyl alcohols, and substituted or unsubstituted heteroarylalkyl alcohols. Preferred are linear alcohols containing 4 or more carbon atoms or aromatic alcohols, when consideration is taken of reaction time and optical purity.

For use in the optical resolution of racemic α-HCCA ester, the enzyme must enantioselectively hydrolyze the ester functionality of a particular isomer of the racemate. Preferably, the enzyme is selected from the group consisting of microorganism- or animal-derived lipases, proteases, and esterases. Depending on enzymes and chemical structures of substrates, the conformation of the α-HCCA hydrolyzed is determined. Also, the selectivity for enantiomers and the enantiomeric excess value of the product are dependent on enzyme and substrate. Such an enantioselective enzyme, when used, may be in a form of a powder or an aqueous solution. The enzyme is preferably used in an amount of 0.1 to 100 parts by weight based on 100 parts by weight of the α-HCCA ester. For example, if the enzyme is used at an amount less than 0.1 part by weight, the hydrolysis may require excessive time to complete. On the other hand, an enzyme amount exceeding 100 parts by weight increases the production cost.

The enzymatic reaction is optimally carried out at 0–60° C. and pH 4–12. As for the organic solvent to extract the remaining enantiomeric α-HCCA ester, it is preferably selected from the group consisting of ethyl acetate, dichloromethane, chloroform, carbon tetrachloride, toluene and mixtures thereof.

Turning now to the reduction of the prepared enantiomeric α-HCCA ester to a corresponding conformation of α-HCCA, two methods are provided for converting an optically pure S- or R-form of α-HCCA ester to a corresponding conformation of α-HCCA with high enantiomeric excess (>99%), in accordance with the present invention.

First, a solution of the recovered S- or R-form of the α-HCCA ester in an organic solvent is subjected to hydrogenation in the presence of palladium catalyst on carbon (Pd/C) under a constant hydrogen partial pressure at a constant temperature.

In this regard, the palladium catalyst is preferably used in an amount of 0.1–30% by weight and more preferably in an amount of 0.5–10% by weight. For example, an amount less than 0.1% by weight is insufficient to perform the hydrogenation. On the other hand, an amount larger than 30% by weight has negative influence on the production cost. The catalytic hydrogenation of the enantiomeric α-HCCA ester is preferably carried out at a hydrogen partial pressure of 1 to 10 bars and more preferably at a hydrogen partial pressure of 1 to 5 bars. For example, the hydrogenation, when being carried out at a hydrogen partial pressure less than 1 bar, is significantly deteriorated in efficiency. On the other hand, a hydrogen partial pressure larger than 10 bars results in formation of a lot of side products. Other conditions are set at 1 to 20 hours and preferably at 1 to 8 hours for reaction time and at 0 to 70° C. and preferably at 20 to 40° C. for reaction temperature.

Of THFA esters, THFA benzyl ester can allow THFA to be recovered therefrom with very high ease. For example, a solution of THFA benzyl ester in an organic solvent is hydrogenated at a constant temperature under a constant hydrogen partial pressure to produce THFA and toluene and simple vacuum distillation removes the toluene, leaving THFA only.

An alternate method is to use an enzyme capable of non-enantioselectively hydrolyzing the ester functionality of the recovered optical isomer of the α-HCCA ester with maintenance of a constant pH and temperature. The enzyme, when used in the non-enantioselective hydrolysis, may be in a form of a powder or an aqueous solution.

After completion of the enzymatic hydrolysis, the aqueous phase is collected and adjusted to pH 2–3 with HCl. Several extractions of the acidified aqueous phase with an organic solvent yield a highly pure S- or R-form of α-HCCA.

A better understanding of the present invention may be obtained in light of the following examples which are set forth to illustrate, but are not to be construed to limit the present invention.

EXAMPLE 1

Screening of Enzyme for Specificity for THFA Ethyl Ester

After being well mixed, 0.1 mole of THFA and 0.3 mole of ethyl alcohol were reacted at 70° C. for 1 hour in the presence of 0.15 mole of thionyl chloride to produce THFA ethyl ester.

To 500 μl of a 50 mM phosphate buffer (pH 7.0), THFA ethyl ester and a hydrolyzing enzyme were added at amounts of 1% and 0.1%, respectively and the resulting reaction was incubated at 30° C. for 30 hours. After completion of the hydrolysis, 50 μl of the reaction was well mixed with an equal volume of 1 N HCl and added with 200 μl of ethyl acetate to extract the remaining substrate. The extract was analyzed by gas chromatography (GC) on a HP-5 column at a temperature range from 80 to 200° C. and by chiral gas chromatography (GC) on a βP-dextrin GC column at a temperature range from 110 to 200° C.

Analysis results are summarized in Table 1, below. As seen in Table 1, the remaining α-HCCA ethyl ester existed as either an R-form, an S-form or a racemate, depending on the enantioselectivity of the enzymes. Therefore, it is confirmed that different enantiomers of THFA ethyl ester can be prepared according to choice of enzyme.

TABLE 1

| Kind | Enzyme Source | Optical Purity (ee %) THFA-C2 | THFA | Chiral Form (THFA Ethyl Ester) | Note |
|---|---|---|---|---|---|
| Protease | Papain | | | | Unreacted |
| | Bacillus subtilis | 27.7% | 51.2% | S | |
| | Aspergillus oryzae | 30.1% | 22.3% | S | |
| | Aspergillus saitoi | | | | Unreacted |
| | Rhizopus. sp | | | | Unreacted |
| | Bacillus licheniformis | 26% | 13.2% | S | |
| | Bacillus amyloliquefaciens | 0% | | | Unreacted |
| Lipase | Candida cylindracea | 88% | 12.3% | | |
| | Aspergillus oryzae | 15.4% | 5.6% | R | |
| | Fongipase | 12.2% | 9.3% | R | |
| | Pseudomonas sp. (immobilized) | 35.3% | 5.7% | S | |
| | Pseudomonas sp. | 3.1% | 0.2% | R | |
| | Candida sp. | 21.5% | 2.5% | R | |
| | Porcine pancreatic | 93.1% | 19.8% | S | |
| | Candida antarctica, fraction B | | | | |
| | Novo IM lipase | 6.2% | 2.5% | R | |
| | Candida rugosa | 0% | | | |
| | Rhizomucor miehei | 13.5% | 1.1% | R | |
| | K80 lipase | 7.6% | 8.2% | S | |
| | L1 lipase | | | | Unreacted |
| | L62 lipase | 16.9% | 10.5% | S | |
| Esterase | Porcine liver | 0% | | | Unreacted |

$$ee \% = \frac{R-S}{R+S} \times 100$$

wherein R and S mean total molar concentrations of R-form and S-form enantiomers, respectively.

EXAMPLE 2
Screening of Enzyme for Specificity for THFA Butyl Ester 0.1 mole of THFA was reacted with 0.1 mole of butyl alcohol at 120° C. for 4 hours in 0.15 mole of toluene in the presence of $1 \times 10^{-4}$ mole of p-toluenesulfonic acid to produce THFA butyl ester.

To 500 µl of a 50 mM phosphate buffer (pH 7.0), THFA ethyl ester and a hydrolyzing enzyme were added at amounts of 1% and 0.1%, respectively, followed by incubation at 30° C. for 16 hours. After completion of the hydrolysis, the substrate was extracted and analyzed in the same manner as in Example 1.

Analysis results are summarized in Table 2, below. As apparent from data of Table 2, the remaining α-HCCA ethyl ester existed as either an R-form, an S-form or a racemate, depending on the enantioselectivity of the enzymes. Therefore, it is confirmed that different enantiomers of THFA ethyl ester can be prepared according to the choice of enzyme.

TABLE 2

| Kind | Enzyme Source | Optical Purity (ee %)[1] THFA-C4 | THFA | Chiral Form (THFA Butyl Ester) | Note |
|---|---|---|---|---|---|
| Protease | Papain | | | | Unreacted |
| | Bacillus subtilis | 16.8% | 37.8% | S | |
| | Aspergillus niger | 100% | 40.5% | R | |
| | Aspergillus oryzae | 100% | 24.6% | S | |
| | Aspergillus saitoi | 5.6% | 27.8% | R | Weakly reacted |
| | Rhizopus. sp | | | | Unreacted |
| | Bacillus licheniformis | 100% | 29.8% | S | |
| | Bacillus amyloliquefaciens | | | | Unreacted |
| Lipase | Candida cylindracea | 88% | 12.3% | R | |
| | Aspergillus oryzae | 79.3% | 0.6% | R | |
| | Fongipase | 76.15% | 2.7% | R | |
| | Pseudomonas sp. (immobilized) | 35.3% | 5.7% | S | |
| | Pseudomonas sp. | 19.1% | 3.7% | S | |
| | Candida sp. | 65.8% | 14.1% | R | |
| | Porcine pancreatic | 35.7% | 20.3% | S | |
| | Candida antarctica, fraction B | 16.1% | 11.3% | R | |
| | Novo IM lipase | 100% | 2.96% | R | |

TABLE 2-continued

| Kind | Enzyme Source | Optical Purity (ee %)[1] THFA-C4 | THFA | Chiral Form (THFA Butyl Ester) | Note |
|---|---|---|---|---|---|
| | Candida rugosa | 81% | 6% | R | |
| | Rhizomucor miehei | | | | Unreacted |
| | K80 lipase | 51.4% | 11% | S | |
| | L1 lipase | 47.1% | 16.3% | R | |
| | L62 lipase | 81.5% | 8.4% | S | |
| Esterase | Porcine liver | 42.2% | 25.3% | R | |

$$ee\ \% = \frac{R-S}{R+S} \times 100$$

wherein R and S mean total molar concentrations of R-form and S-form enantiomers, respectively.

EXAMPLE 3
Screening of Enzyme for Specificity for THFA Benzyl Ester

THFA benzyl ester was prepared in a manner similar to that of Example 1, except that benzyl alcohol was used.

To 500 μl of a 50 mM phosphate buffer (pH 7.0), THFA benzyl ester and a hydrolyzing enzyme were added at amounts of 1% and 0.1%, respectively and the resulting reaction was incubated at 30° C. for 16 hours. After completion of the hydrolysis, the substrate was extracted and analyzed in the same manner as in Example 1.

Analysis results are summarized in Table 3, below. As apparent from data of Table 3, the remaining α-HCCA benzyl ester existed as either an R-form, an S-form or a racemate, depending on the enantioselectivity of the enzymes. Therefore, it is confirmed that different enantiomers of THFA ethyl ester can be prepared according to the choice of enzyme.

EXAMPLE 4
Separation of THFA Ester and THFA Using Organic Solvent

Racemic THFA ester was enantioselectively hydrolyzed by an enzyme and an organic solvent was added to the enzyme reaction to separate the R- or S-form of the product THFA from the corresponding S- or R-form of the substrate remaining unhydrolyzed as follows.

R, S-THFA butyl ester and *Bacillus licheniformis* protease were added at amounts of 2% and 1%, respectively, to 1 liter of a 50 mM phosphate buffer (pH 7.0) and the resulting reaction was incubated at 30° C. for 4 hours under a condition of pH 7. After completion of the hydrolysis, the substrate was extracted and analyzed in the same manner as in Example 1.

The remainder of the reaction was added with 500 ml of ethyl acetate and mixed well, followed by phase separation to recover the organic layer. The aqueous layer was extracted

TABLE 3

| Kind | Enzyme Source | Optical Purity (ee %)[1] THFA-Bz | THFA | Chiral Form (THFA Benzyl Ester) | Note |
|---|---|---|---|---|---|
| Protease | Papain | | | | Unreacted |
| | Bacillus subtilis | 94.7% | 31.8% | S | |
| | Aspergillus oryzae | 98.3% | 26.5% | S | |
| | Aspergillus saitoi | 22.2% | 19.9% | S | |
| | Rhizopus. sp | 38.4% | 44.1% | S | |
| | Bacillus licheniformis | 91.5% | 29.1% | S | |
| | Bacillus amyloliquefaciens | 83.6% | 36% | S | |
| Lipase | Candida cylindracea | 0.7% | 5.8% | — | |
| | Aspergillus oryzae | 18.1% | 22% | R | |
| | Fongipase | 0% | | | |
| | Pseudomonas sp. (immobilized) | 13.1% | 21.9% | S | |
| | Pseudomonas sp. | 1.8% | 9.5% | S | |
| | Candida sp. | 0% | | | |
| | Porcine pancreatic | 0% | | | |
| | Candida antarctica, fraction B | 35% | 10.7% | S | |
| | Novo IM lipase | 78.3% | 3.9% | R | |
| | Candida rugosa | 0% | | | |
| | Rhizomucor miehei | 0% | | | |
| | K80 lipase | 92.1% | 20.4% | S | |
| | L1 lipase | 40% | 6% | R | |
| | L62 lipase | 0% | | | |
| Esterase | Porcine liver | 0% | | | |

$$ee\ \% = \frac{R-S}{R+S} \times 100$$

wherein R and S mean total molar concentrations of R-form and S-form enantiomers, respectively.

one more time with 500 ml of ethyl acetate and the ethyl acetate layers obtained were pooled. This pooled organic layer was dehydrated over 5 g of sodium sulfate. Vacuum distillation removed the ethyl acetate, leaving 9.6 g of S-THFA butyl ester which was measured to be 99.4% in enantiomeric excess. The THFA remaining in the aqueous phase was identified to be an R-form with 70% enantiomeric excess.

EXAMPLES 5 TO 13

Change in Enantiomeric Excess According to Ratio of Enzyme: Substrate, Temperature, and pH The same procedure as in Example 4 was conducted, except that the concentration of R, S-THFA butyl ester was fixed at 8% by weight while varying the ratio of enzyme:substrate, reaction temperature, and pH. Results are given in Table 4, below.

TABLE 4

| Example No. | Enz.: Sub | Rxn Time (hr) | Rxn Temp. (° C.) | Optical Purity (ee%) | pH |
| --- | --- | --- | --- | --- | --- |
| 5 | 1:2 | 5 | 50 | 100 | in-constant |
| 6 | 1:2 | 2 | 50 | 98.6 | 7 |
| 7 | 1:4 | 3.5 | 50 | 98.4 | 7 |
| 8 | 1:8 | 7.5 | 50 | 98.9 | 7 |
| 9 | 1:4 | 4 | 50 | 98.6 | 9 |
| 10 | 1:8 | 4 | 50 | 98.5 | 9 |
| 11 | 1:8 | 4 | 30 | 98.7 | 9 |
| 12 | 1:12 | 8.5 | 30 | 98.8 | 9 |
| 13 | 1:16 | 11 | 30 | 97.4 | 9 |

EXAMPLE 14

Optical Resolution of Butyl Ester Using *Bacillus licheniformis* Protease

To 400 ml of a 50 mM phosphate buffer (pH 9.0) were added 12% by weight of R, S-THFA butyl ester and 1% by weight of *Bacillus licheniformis* protease and the resulting incubated at 30° C. for 10.5 hours with reaction of pH 9.0. After completion of the hydrolysis, the substrate was extracted and analyzed in the same manner as in Example 1.

Using 200 ml of ethyl acetate, 21 g of S-THFA butyl ester was obtained in the same manner as in Example 4, and analyzed to be 99.3% in enantiomeric excess. The THFA remaining in the aqueous phase was identified to be an R-form with 60% enantiomeric excess.

EXAMPLE 15

Optical Resolution of Butyl Ester Using *Bacillus licheniformis* Protease 12 g of S-THFA butyl ester was prepared in a manner similar to that of Example 14, except that 200 ml of a 50 mM phosphate buffer (pH 9.0) was used at 20° C. for the hydrolysis and 100 ml of ethyl acetate was added for substrate separation, and its optical purity was measured to be 99.3% in enantiomeric excess.

EXAMPLE 16

Optical Resolution of Butyl Ester Using *Bacillus licheniformis* Protease 21 g of S-THFA butyl ester was prepared in a manner similar to that of Example 14, except that the hydrolysis was carried out at 10° C. for 19 hours, and its optical purity was measured to be 99.1% in enantiomeric excess.

EXAMPLE 17

Optical Resolution of Butyl Ester Using *Bacillus licheniformis* Protease 25.7 g of S-THFA butyl ester was prepared in a manner similar to that of Example 14, except that the hydrolysis was carried out at 20° C. for 26 hours with 15% by weight of R, S-THFA butyl ester in 200 ml of a 50 mM phosphate buffer (pH 9.0) and 100 ml of ethyl acetate was added for substrate separation, and its optical purity was measured to be 99.8% in enantiomeric excess.

EXAMPLES 18 TO 22

Optical Resolution of Butyl Ester Using *Bacillus licheniformis* Protease

S-THFA butyl ester was prepared under the same conditions as in Example 17 while varying concentrations of R, S-THFA butyl ester and the ratio of enzyme to substrate according to the conditions given in Table 5, below. Analysis results are also given in Table 5.

TABLE 5

| Example No. | Sub. Conc. | Enz.: Sub | Rxn Time (hr) | Yield (%) | ee % |
| --- | --- | --- | --- | --- | --- |
| 18 | 15% | 1:12 | 21 | 25.5 | 100 |
| 19 | 30% | 1:12 | 24 | 30 | 99 |
| 20 | 30% | 1:15 | 26 | 33.7 | 99.2 |
| 21 | 40% | 1:15 | 28 | 46.4 | 99.1 |
| 22 | 50% | 1:12 | 30 | 50 | 98.9 |

EXAMPLE 23

Optical Resolution of THFA

A butyl ester racemate was prepared in the same manner as in Example 3. To 200 ml of a 50 mM phosphate buffer (pH 9.0) were added 12% by weight of the prepared R, S-THFA benzyl ester and 1% by weight of *Bacillus licheniformis* protease and the resulting reaction was incubated at 20° C. for 4.5 hours with maintenance of pH 9.0. After completion of the hydrolysis, the reaction was analyzed as in Example 1. The remainder of the reaction was added with 100 ml of ethyl acetate and mixed well, after which 16 g of S-THFA benzyl ester was obtained in the same manner as in Example 14 and identified to be 99.1% in enantiomeric excess.

In 20 ml of ethyl acetate was dissolved 55 g of the obtained S-THFA benzyl ester and added 55 mg (1% by weight) of 10% palladium catalyst (Pd/C), followed by stirring the solution at room temperature for 10 min. Hydrogen gas was fed into the reaction little by little to a hydrogen partial pressure of 1.5 bars at which point stirring was resumed for 10 hours. After removal of the palladium catalyst through filtration, vacuum distillation of the ethyl acetate and produced toluene left 2.5 g of S-THFA. This enantiomeric compound was found to be 99.1% in enantiomeric excess as measured by chiral GC.

EXAMPLE 24

Preparation of S-THFA from S-THFA Butyl Ester

In the presence of *Candida antarctica*, fraction B lipase, which was demonstrated to non-enantioselectively hydrolyze R, S-THFA butyl ester in Example 2, S-THFA butyl ester was hydrolyzed to S-THFA without using strong acid and strong base nor producing isomers.

To 300 ml of a 50 mM phosphate buffer (pH 7.0) were added 1% by weight of S-THFA butyl ester and 0.1% by weight of *Candida antarctica,* fraction B lipase and the resulting reaction was incubated at 30° C. for 1 hour. After completion of the hydrolysis, the substrate was extracted and analyzed in the same manner as in Example 1.

GC analysis confirmed the hydrolysis of all S-THFA butyl ester to THFA which was found to be 99.8% in enantiomeric excess as measured by chiral GC.

EXAMPLES 25–33

Preparation of S-THFA from S-THFA Butyl Ester

The procedure of Example 24 was carried out using different enzymes, and the results are given in Table 6, below.

TABLE 6

| Example No. | Enzyme | Rxn Time (hr) | ee % (S-THFA) |
|---|---|---|---|
| 25 | *Aspergillus oryzae* lipase | 16 | 100 |
| 26 | Fongipase | 16 | 100 |
| 27 | Pseudomonas sp. Lipase (immobilized) | 16 | 100 |
| 28 | Pseudomonas sp. Lipase | 16 | 100 |
| 29 | Candida sp. Lipase | 1.5 | 100 |
| 30 | *Candida antarctica,* fraction B Lipase | 1 | 100 |
| 31 | Novo IM Lipase | 5 | 100 |
| 32 | L62 lipase | 2.5 | 100 |
| 33 | Porcine liver Esterase | 0.15 | 100 |

EXAMPLE 34

Optical Resolution of THFA

To 200 ml of a 50 mM phosphate buffer (pH 9.0) were added 12% by weight of R, S-THFA butyl ester and 1% by weight of *Bacillus licheniformis* protease and the resulting reaction was incubated at 20° C. for 10.5 hours with maintenance of pH 9.0. After the hydrolysis, the reaction was analyzed as in Example 1. After the remainder of the reaction was added with 100 ml of ethyl acetate and mixed well, 12 g of S-THFA butyl ester was obtained in the same manner as in Example 14 and identified to be 99.3% in enantiomeric excess.

In 100 ml of a 50 mM phosphate buffer (pH 7.0), 12 g of the prepared S-THFA butyl ester was hydrolyzed at 30° C. for 5 hours in the presence of 1 g of *Candida antarctica,* fraction B lipase with maintenance of pH 7.0. Following the hydrolysis, the reaction results were analyzed as in Example 1. The remainder of the reaction was adjusted to pH 2.0 with HCl, followed by three extractions with 3 volumes of ethyl acetate. After the ethyl acetate extracts were pooled, 6 g of S-THFA was recovered from the pool in the same manner as in Example 14. The compound was found to be 99.3% in enantiomeric excess as measured by chiral GC.

EXAMPLE 35

Mass-Scale Optical Resolution of THFA

To 2 liters of a 50 mM phosphate buffer (pH 9.0) were added 40% by weight of R, S-THFA butyl ester and 3% by weight of *Bacillus licheniformis* protease and the resulting reaction was incubated at 20° C. for 23 hours with maintenance of pH 9.0. After the hydrolysis, the reaction was analyzed as in Example 1. After the remainder of the reaction was added with 1 liter of ethyl acetate and mixed well, 400 g of S-THFA butyl ester was obtained in the same manner as in Example 14 and identified to be 99.3% in enantiomeric excess.

In 400 ml of a 50 mM phosphate buffer (pH 7.0), 160 g of the prepared S-THFA butyl ester was hydrolyzed at 30° C. for 6 hours in the presence of 8 g of *Candida antarctica,* fraction B lipase with maintenance of pH 7.0. Following the hydrolysis, the reaction results were analyzed as in Example 1. The remainder of the reaction was adjusted to pH 2.0 with HCl, followed by three extractions with 3 volumes of ethyl acetate. After the ethyl acetate extracts were pooled, 80 g of S-THFA was recovered in the same manner as in Example 14. The compound was found to be 99.3% in enantiomeric excess as measured by chiral GC.

As described hereinbefore, a racemic mixture of α-HCCA can be optically resolved with high optical purity at high yields in accordance with the present invention. Additionally, the present invention is economically favorable because such chiral compounds can be produced at low cost.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for optically resolving a racemic α-substituted heterocyclic carboxylic acid, comprising the steps of:

reacting a racemic α-substituted heterocyclic carboxylic acid with alcohol to give a racemic α-substituted heterocyclic carboxylic acid ester having the following chemical formula 1:

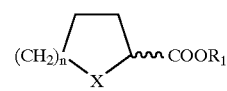

1 wherein, $R_1$ is selected from the group consisting of substituted or unsubstituted alkyl or alkenyl containing 1 to 6 carbon atoms, benzyl, cycloalkyl containing 3 to 6 carbon atoms, substituted or unsubstituted arylalkyl, and substituted or unsubstituted heteroarylalkyl, X represents O, S or NH, and n is an integer of 1 to 3;

optically resolving the racemate of the formula 1 in an aqueous solution by use of an enzyme with enantioselectivity to hydrolyze either R-form or S-form of the racemate, thereby producing an R-form or S-form of α-substituted heterocyclic carboxylic acid and a counter enatiomeric form of α-substituted heterocyclic carboxylic acid ester thereto, said enzyme existing as a powder or an aqueous solution;

extracting the unhydrolyzed α-substituted heterocyclic carboxylic acid ester of the racemate with an organic solvent, followed by recovering the α-substituted heterocyclic carboxylic acid ester from the organic phase and the α-substituted heterocyclic carboxylic acid from the aqueous phase, respectively; and subjecting the recovered α-substituted heterocyclic carboxylic acid ester in an organic solvent to hydrogenation under a constant hydrogen partial pressure at a constant temperature in the presence of a palladium catalyst on carbon (Pd/C), followed by recovering the resulting α-substituted heterocyclic carboxylic acid.

2. The method as set forth in claim 1, wherein said alcohol is selected from the group consisting of linear or branched alcohols containing 1 to 6 carbon atoms, aromatic alcohols, cycloalkyl alcohols containing 3 to 6 carbon atoms, substituted or unsubstituted arylalkyl alcohols, and substituted or unsubstituted heteroarylalkyl alcohols.

3. The method as set forth in claim 1, wherein said enzyme is derived from microorganisms or animals and selected from the group consisting of lipases, proteases and esterases.

4. The method as set forth in claim 1, wherein said enzyme is used in an amount of 0.1 to 100 parts by weight based on 100 parts by weight an assemble for α-substituted heterocyclic carboxylic acid.

5. The method as set forth in claim 1, wherein said optical resolving step is carried out in an aqueous solution at 0 to 60° C. with maintenance of pH at 4 to 12.

6. The method as set forth in claim 1, wherein said organic solvent is selected from the group consisting of ethyl acetate, dichloromethane, chloroform, carbon tetrachloride, toluene, and mixtures thereof.

7. The method as set forth in claim 1, wherein said palladium catalyst is used in an amount of 0.1 to 30% by weight.

8. The method as set forth in claim 1, wherein said hydrogen partial pressure is maintained within the range of 1 to 10 bars and the hydrogenation is carried out at 0 to 70° C.

9. A method for optically resolving a racemic α-substituted heterocyclic carboxylic acid, comprising the steps of:

reacting a racemic α-substituted heterocyclic carboxylic acid with alcohol to give a racemic α-substituted heterocyclic carboxylic acid ester having the following chemical formula 1:

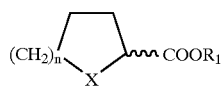

1 wherein, $R_1$ is selected from the group consisting of substituted or unsubstituted alkyl or alkenyl containing 1 to 6 carbon atoms, benzyl, cycloalkyl containing 3 to 6 carbon atoms, substituted or unsubstituted arylalkyl, and substituted or unsubstituted heteroarylalkyl, X represents O, S or NH, and n is an integer of 1 to 3;

optically resolving the racemate of the formula 1 in an aqueous solution by use of an enzyme with enantioselectivity to hydrolyze either R-form or S-form of the racemate, thereby producing an R-form or S-form of α-substituted heterocyclic carboxylic acid and a counter enatiomeric form of i-substituted heterocyclic carboxylic acid ester thereto, said enzyme existing as a powder or an aqueous solution;

extracting the unhydrolyzed α-substituted heterocyclic carboxylic acid ester of the racemate with an organic solvent, followed by recovering the α-substituted heterocyclic carboxylic acid ester from the organic phase and the α-substituted heterocyclic carboxylic acid from the aqueous phase, respectively; and hydrolyzing the recovered α-substituted heterocyclic carboxylic acid ester with a non-enantioselective enzyme in an aqueous solution at a constant pH and temperature, said enzyme existing as a powder or an aqueous solution, followed by recovering the resulting α-substituted heterocyclic carboxylic acid.

10. The method as set forth in claim 9, wherein said alcohol is selected from the group consisting of linear or branched alcohols containing 1 to 6 carbon atoms, aromatic alcohols, cycloalkyl alcohols containing 3 to 6 carbon atoms, substituted or unsubstituted arylalkyl alcohols, and substituted or unsubstituted heteroarylalkyl alcohols.

11. The method as set forth in claim 9, wherein said enzyme is derived from microorganisms or animals and selected from the group consisting of lipases, proteases and esterases.

12. The method as set forth in claim 9, wherein said enzyme with enantioselectivity is used in an amount of 0.1 to 100 parts by weight based on 100 parts by weight of α-substituted heterocyclic carboxylic acid.

13. The method as set forth in claim 9, wherein said optical resolving step is carried out in an aqueous solution at 0 to 60° C. with maintenance of pH at 4 to 12.

14. The method as set forth in claim 9, wherein said organic solvent is selected from the group consisting of ethyl acetate, dichloromethane, chloroform, carbon tetrachloride, toluene, and mixtures thereof.

15. The method as set forth in claim 3, wherein said enzyme is used in an amount of 0.1 to 100 parts by weight based on 100 parts by weight of α-substituted heterocyclic carbocyclic acid.

* * * * *